United States Patent [19]

Hart

[11] Patent Number: 4,947,885

[45] Date of Patent: Aug. 14, 1990

[54] BRINE MONITOR

[75] Inventor: Paul R. Hart, The Woodlands, Tex.

[73] Assignee: Betz Laboratories, Inc., Trevose, Pa.

[21] Appl. No.: 386,545

[22] Filed: Jul. 27, 1989

[51] Int. Cl.$^5$ .............................................. B01D 17/04
[52] U.S. Cl. ......................................... 137/5; 137/93; 252/328
[58] Field of Search ................. 137/5, 93, 2; 252/328, 252/329, 330

[56] References Cited

U.S. PATENT DOCUMENTS

| | | | |
|---|---|---|---|
| 3,220,930 | 11/1965 | Thompson | 252/328 X |
| 3,256,902 | 6/1966 | Porter | 252/328 X |
| 3,410,292 | 11/1968 | Bennett et al. | 137/93 |
| 3,592,212 | 7/1971 | Schleimer et al. | 137/93 |
| 3,899,688 | 8/1975 | Perieres | 250/576 |
| 4,128,833 | 12/1978 | Tsavaris | 340/603 |
| 4,273,146 | 6/1981 | Johnson | 137/5 |
| 4,323,092 | 4/1982 | Zabel | 137/5 |

FOREIGN PATENT DOCUMENTS

| | | | |
|---|---|---|---|
| 916531 | 3/1981 | U.S.S.R. | 252/328 |
| 916532 | 3/1982 | U.S.S.R. | 252/328 |

*Primary Examiner*—Alan Cohan
*Attorney, Agent, or Firm*—Alexander D. Ricci; Gregory M. Hill

[57] ABSTRACT

In the desalter operation of a petroleum refinery, a method which measures and regulates the stability of the oil-in-water emulsion. A device located downstream of the desalter monitors the electrical charge of oil droplets in the effluent brine. This charge reflects emulsion stability. The amount of charge streaming past a point defines a current. When a predetermined streaming current threshold is crossed, the monitoring device electrically sends a signal proportional to the excess to a metering pump or valve which adds a predetermined proportional quantity of emulsion breaker to the petroleum/water mixture in the desalter.

9 Claims, No Drawings

BRINE MONITOR

FIELD OF THE INVENTION

The present invention relates to the petroleum refining industry and more specifically to the monitoring of the effluent water from the desalter operation.

BACKGROUND OF THE INVENTION

The art of monitoring and responding to changes in the chemical make-up of an aqueous medium has traditionally included various and sometimes diverse methods. Of particular interest herein are the methods used to monitor the aqueous, sometimes called brine, effluent from the desalter operation of a petroleum refinery.

Crude oil desalting is a common emulsion breaking application where the emulsion is first intentionally formed. Water is added in an amount of approximately between 3% and 8% by volume of crude. The added water is intimately mixed with the crude oil to contact the impurities therein, thereby transferring these impurities into the water phase of the emulsion. The emulsion is usually resolved with the assistance of emulsion breaking chemicals, which are characteristically surfactants, and by the known method of providing an electrical field to polarize the water droplets. Once the emulsion is broken, the water and petroleum media form distinct phases. The water phase is separated from the petroleum phase and subsequently removed from the desalter. The petroleum phase is directed further downstream for processing through the refinery operation.

The efficiency of the desalting operation is, in part, dependent upon the proper handling of the emulsion. A precise amount of emulsion breakers is essential. Specifically, either too little or too much breaker can stabilize an emulsion. This is characterized by increased opaqueness of the effluent. Common contemporary devices monitor the level of opaqueness of the brine effluent. However, this method does not differentiate between undertreatment and overtreatment. This can result in serious operational problems. An improper reading of the emulsion could result, for example, to the addition of more emulsion breakers to an emulsion already overtreated which would, in turn, lead to further emulsion stabilization and loss of system control.

PRIOR ART

Various devices exist which qualitatively and quantitatively measure different elements and conditions present in liquid media. Particularly relevant, and characteristic of the state of the art, is U.S. Pat. No. 3,899,688, Perieres. The patent discloses a process whereby a photoelectric device is used to monitor the hydrocarbon content of waste water rejected by sea-faring tankers. The detection device is electrically connected to means for directing the water either to the sea or to a slop tank for further processing. The detection device is also connected to a mechanical emulsifying means and is intended to maintain a stable hydrocarbon in water emulsion.

U.S. Pat. No. 4,128,833, Tsavaris, also discloses the use of a photoelectric device to monitor the introduction of oil pollution into a feedwater system. The monitoring device triggers alarm systems when the level of oil is detected to exceed a minimum threshold value.

There are various factors within an aqueous environment which photoelectric devices cannot detect, such as pH values. U.S. Pat. No. 3,410,292, Bennett, et al., disclose a method of monitoring and controlling the pH of a liquid by immersing probes into the liquid capable of sensing the electrical conductivity of the liquid. In this manner, pH is monitored. The device is capable of being connected to means for adding a component to the liquid medium for the purpose of returning the pH to a predetermined value.

In U.S. Pat. No. 3,592,212, Schleimer et al., the previously mentioned concept is expanded. Schleimer et al., disclose an electrical detection device useful in water treatment systems which is capable of monitoring pH and dissolved solids (to determine corrosion rates). A master scanner circuit receives input from the monitoring devices and determines what response, if any, is needed to correct an imbalanced condition.

Johnson, in U.S. Pat. No. 4,273,146, discloses monitoring electrical conductivity, as a function of the salts concentration, to determine pH values. Variations in the pH and salts concentration are corrected by a timed, controlled volume release of water from the system.

Of lesser interest is U.S. Pat. No. 4,323,092, Zabel, which discloses electrodes being introduced into the aqueous medium of the circulation system of, for example, a swimming pool for the purpose of monitoring the chlorine content of the aqueous medium. The output signal from the electrodes is directed to a control means which regulates a mechanism to meter the appropriate amount of chlorine into the aqueous medium.

DETAILED DESCRIPTION OF THE INVENTION

The present invention consists of a method of monitoring an aqueous medium encapsulated by and continuously flowing through a tube-like structure. It has exceptional utility in a petroleum refinery to monitor the condition of the effluent brine from the desalter operation. The amount of hydrocarbons present in the effluent brine reflects the level of efficiency of the emulsion breaking function in the desalter. An increasing amount of hydrocarbon in the effluent indicates increasing stability in the emulsion. Such a condition is undesirable and, once detected, must be corrected.

The present invention detects the hydrocarbon content of the effluent brine by means of a sensor which monitors the electrical charge density of the oil droplets in the brine. The sensor is a streaming current detector and is commercially available from such sources as, for example, Milton Roy under the product name of Generation II Coagulant Control Center.

A probe from the streaming current detector is inserted through the wall of the tubing which carries the effluent brine away from the desalter. In this way, the probe is in intimate contact with the effluent brine.

The stability of the emulsion is a function of the electrical charge of the emulsion particles. Charge neutralization is a necessary condition for destabilizing the emulsion. Since emulsion destabilization is necessary for the proper functioning of the desalter, the maintenance of a neutral charge is required.

The streaming current detector monitors the charge of the effluent brine. It automatically computes the streaming current which is calculated as follows:

Emulsion's surface density of charge (Zeta potential) ×

Surface area per volume × Volumetric flow rate

When the streaming current detector records a negative streaming current, it will send an electrical signal proportional to that current to a mechanism such as a pump, solenoid controlled valve or any similar known device for the purpose of metering a predetermined proportional amount of cationic emulsion breaker into the desalter vessel, wash water or any other convenient and appropriate location within the desalter system, such as the mud wash. The cationic breaker may be fed continuously or shot fed intermittently, as required. If on a continuous basis, the streaming current detector will signal the addition of cationic breaker at a predetermined proportional feedrate. The more negative the streaming current, the greater will be the feedrate of cationic breaker. With less negative streaming current, the feedrate of cationic breaker will therefore be less. Although petroleum emulsions in water are naturally anionic, in the event of a cationic emulsion, an anionic breaker can be similarly controlled. Noionic breakers can be added in a complementary fashion in order to maintain a more constant chemical feedrate.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

I claim:

1. In a petroleum refinery desalter a method for measuring the hydrocarbon content of the effluent brine from said desalter comprising disposing a probe within said effluent brine to detect and quantitatively measure an electrical charge therein and to direct an output electrical signal incorporation to said electrical charge to means for adding a pre-determined amount of a chemical compound to the fluid contents of said desalter, the amount of said chemical compound being infinitely variable inproportion to variations in said output electrical signal.

2. A method according to claim 1 wherein said effluent brine is an oil-in-water emulsion.

3. A method according to claim 1 wherein said substantially aqueous medium is effluent brine from said desalter.

4. A method according to claim 1 wherein said electrical charge is used to measure the variable stability of said emulsion over time.

5. A method according to claim 1 wherein said means for adding said chemical compound comprises a pump.

6. A method according to claim 1 wherein said means for adding said chemical compound comprises an electrically activated flow valve.

7. A method according to claim 1 wherein said electrical charge comprises a streaming current.

8. A method according to claim 1 wherein said chemical compond is an emulsion breaker.

9. A method according to claim 1 wherein said probe is a streaming current detector.

* * * * *